United States Patent [19]

Govaert et al.

[11] Patent Number: 4,632,123
[45] Date of Patent: Dec. 30, 1986

[54] RADIOACTIVITY DETECTION SYSTEM

[75] Inventors: Johan A. Govaert; Joseph E. Town, both of Peabody, Mass.

[73] Assignee: Baird Corporation, Bedford, Mass.

[21] Appl. No.: 609,005

[22] Filed: May 10, 1984

Related U.S. Application Data

[62] Division of Ser. No. 369,654, Apr. 19, 1982.

[51] Int. Cl.$^4$ .............................................. A61B 6/00
[52] U.S. Cl. .................................... 128/659; 272/73; 250/363 S; 378/198; 128/654
[58] Field of Search .............. 128/653, 659, 707, 654; 272/73; 378/195, 197, 198, 196

[56] References Cited

U.S. PATENT DOCUMENTS

| | | |
|---|---|---|
| 3,395,698 | 8/1968 | Morehouse ............................ 272/73 |
| 3,465,145 | 9/1969 | Leiter .................................. 128/659 |
| 3,528,407 | 9/1970 | Espagno ............................... 128/654 |
| 3,542,012 | 11/1970 | Frieberger et al. ..................... 272/73 |
| 3,617,749 | 11/1971 | Massiot ................................ 378/198 |
| 3,675,640 | 7/1972 | Gatts ................................... 272/69 |
| 3,890,957 | 6/1975 | Youdin et al. ........................ 128/654 |
| 4,044,332 | 8/1977 | Grenier ................................ 250/369 |
| 4,112,928 | 9/1978 | Putsch .................................. 272/73 |
| 4,166,602 | 9/1979 | Nilsen et al. ......................... 378/197 |
| 4,197,836 | 4/1980 | Wagner et al. ....................... 128/654 |
| 4,211,927 | 7/1980 | Hellstrom et al. .................... 378/197 |
| 4,267,452 | 5/1981 | Govaert ............................... 250/366 |
| 4,387,468 | 6/1983 | Fenne et al. ......................... 378/198 |
| 4,404,973 | 9/1983 | Lancaster et al. .................... 128/654 |

FOREIGN PATENT DOCUMENTS 2717883 11/1978 Fed. Rep. of Germany ...... 128/707

Primary Examiner—Kyle L. Howell
Assistant Examiner—Ruth S. Smith
Attorney, Agent, or Firm—Morse, Altman & Dacey

[57] ABSTRACT

A radioactivity detection system including a crystal detector formed of a unitary body and having two sensing heads. Each sensing head defines a specific address location in a sensing array having a plurality of detectors. A number of detectors are superposed on the sensing array such that activity in one sensing head activates two adjacent detectors, one more than the other. The system further includes means for mounting the detectors for relative motion with respect to a subject and processing means coupled to the detectors. Preferably, the mounting means is operatively connected to an exercising means for stress analysis. Preferably, the mounting means is secured on a movable platform and is connected to the exercising means by a quick connect-disconnect mechanism. In a further embodiment, a detector assembly is designed for rotation about the subject.

3 Claims, 13 Drawing Figures

RADIOACTIVITY DETECTION SYSTEM

This is a division of application Ser. No. 369,654 filed on Apr. 19, 1982.

BACKGROUND OF THE INVENTION

1. Field of the Invention

The present invention relates generally to detecting systems and, more particularly, to a radioactivity detection system and detectors therefor.

2. The Prior Art

Various types of radioactivity distribution measurement systems are known in the art for determining the location of radioactive material injected in diagnostic amounts into a human body or the like. These systems utilize an array of scintillators for sensing radioactive events within the body and a plurality of photomultiplier tubes that are coupled to the scintillators for detecting the sensed events. The address location for each activated scintillator is linearly encoded and then processed to provide a pictorial representation of the relative radioactive event levels detected by the scintillators. Spatial resolution is limited by the smallest diameter of available photomultiplier tubes.

Such systems have suffered from the disadvantages that linear encoding of scintillator address locations requires an excessive number of photomultiplier tubes in order to provide each scintillator with a unique address location. A large number of photomultiplier tubes increases the system costs and increases the likelihood for system downtime. Such systems also suffer from the disadvantage that the dark current of the photomultiplier tubes causes pulses (dark noise) which, in certain instances, are incorrectly interpreted as valid scintillations.

In U.S. Pat. No. 4,267,452, assigned to a common assignee, a system is disclosed in which three photomultiplier tubes are required to determine the position of an activated scintillator. This system shows one photomultiplier tube superposed on four crystal assemblies, with each assembly containing four scintillators. There are thus sixteen scintillators that potentially can provide light signals, in various amounts, to one photomultiplier tube. This in turn requires a rather complex anticoincidence/coincidence logic in the processing of the signals from the photomultiplier tubes.

SUMMARY OF THE INVENTION

It is a principal object of the present invention to overcome the above shortcomings by providing a radioactivity detection system for presentation of radioactive event distributions.

More specifically, it is an object of the present invention to provide a radioactivity detection system that includes a crystal scintillation detector formed of a unitary body and having two sensing heads. Each sensing head defines a specific address location in a sensing array comprising a plurality of crystal scintillation detectors. A number of light detectors are superposed on the sensing array in a manner that activity in one sensing head activates two adjacent light detectors, one more than the other. The system further includes means for mounting the radiation detection array for relative motion to a subject under diagnosis, and processing means coupled to the detectors. Preferably, the mounting means is operatively connected to an exercising means for performing physiologic stress analysis of the subject. Preferably, the mounting means is secured on a movable platform, which is connected to the exercising means by a quick connect-disconnect mechanism. This allows the detection system to be moved expeditiously from the stress analysis area to another location, such as a patient's bedside. In a further embodiment, a detector assembly is designed for rotation about the subject.

The resultant radioactivity detection system is a versatile yet compact, high resolution system, which provides more signal output per each light detector than heretofore attainable and it also allows for simpler processing circuitry than heretofore possible.

Other and further objects of the present invention will in part be obvious and will in part appear hereinafter.

The invention accordingly comprises the radioactivity detection system of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENTS

In general, a radioactivity detection system 10 is used for determining the location and distribution of radioactive events emitted from a subject under diagnosis into which a diagnostic amount of radioactive material has been injected.

Figure 1:
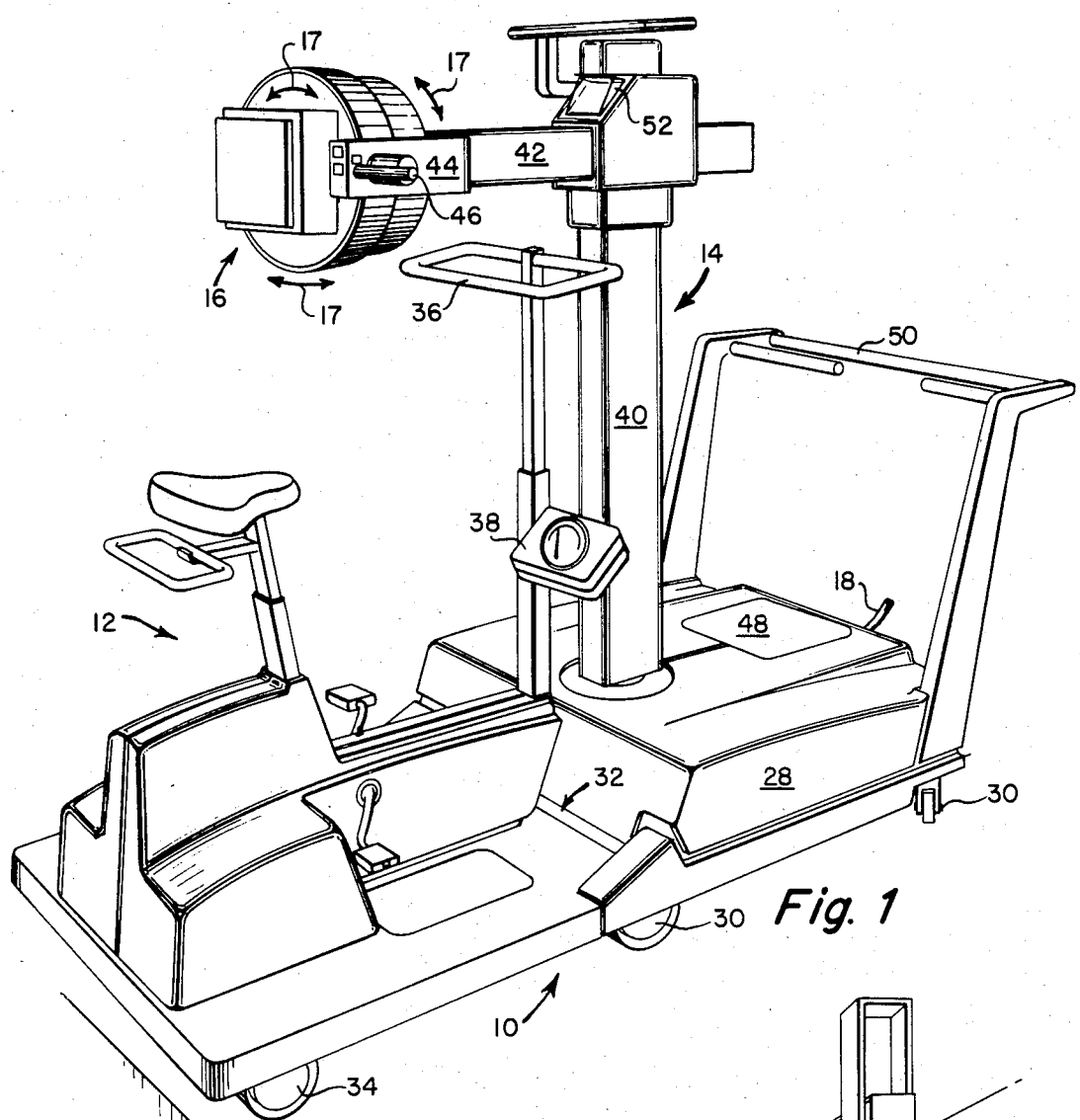
FIG. 1 is a perspective view of one preferred embodiment of a radioactivity detection system constructed in accordance with the present invention.

A perspective view of one preferred embodiment of such a radioactivity detection system 10 is illustrated in FIG. 1. System 10 is a high resolution system specifically designed for physiologic stress analysis, such as heart function, of the subject, not shown. The radioactivity detection system 10 essentially comprises an exercising means 12, a mounting means 14 and a radioactivity distribution detector 16 secured on the mounting means 14. By means of a cable 18, the radioactivity distribution detector 16 is designed to be connected to a suitable processing means 20, such as the one illustrated in FIG. 2. The processing means 20 preferably includes a visual display 22, a graphic recorder 24, and a manual data input terminal 26, such as a keyboard. The exercising means 12 may comprise an exercise bike as shown, or a treadmill, not shown. Preferably, the mounting means 14 is secured on a platform 28 supported on casters 30. In turn, the platform 28 is connected to the exercising means 12 via a suitable quick connect-disconnect mechanism 32, which may take the form of a pair of arms projecting from the exercising means 12 and designed to be received within appropriate depressions formed in the platform 28. The exercising means 12 preferably also is mounted on a pair of wheels 34 so as to be on the same approximate height above the floor as the platform 28. The radioactivity detection system 10 thus can be used for stress analysis of an ambulatory subject, or it can be used for bedside analysis of a bedridden patient.

Figure 3:
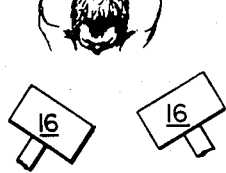
FIG. 3 is a schematic plan view illustrating a dual detection system.
Figure 4:
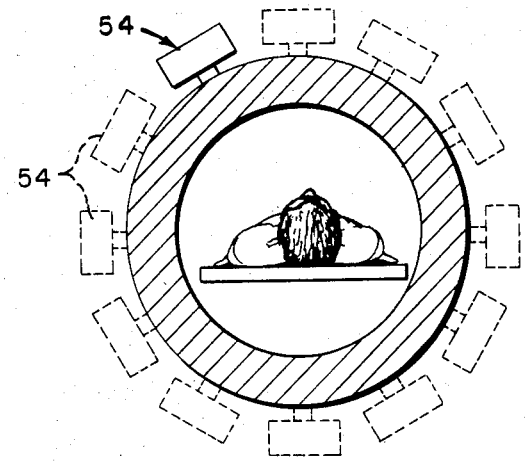
FIG. 4 is a schematic cross section, illustrating another preferred embodiment of the present invention.

The exercising means 12 preferably is provided with a handle bar 36, whose height is adjustable, and a display 38, indicating the level of exertion by the subject. The exercising means 12 preferably is worked such that a subject's position thereon remains fixed about a vertical axis coincident with that of the subject's heart, so that working of the means 12 does not cause lateral displacement of the heart out of the detector's 16 field of view. The detector mounting means 14 preferably is three-dimensionally adjustable so as to allow for the desired positioning of the radioactivity distribution detector 16 with respect to the subject, whether the subject is exercising on the exercising means 12 or is bedridden. To this end, the mounting means 14 preferably comprises a rotatable vertical post 40, carrying a horizontal member 42 for translational motion with respect thereto. At its forward end, the member 42 has journalled thereto a yoke 44, by means of which the detector 16 can be adjusted angularly in all directions, as shown by the arrows 17. Positioning of the detector 16 is effected by a handle 46. When the mounting means 14 is in transport or storage, the detector 16 preferably is made to rest at an area 48 on the platform 28. The platform 28 furthermore is provided with a horizontal bar 50, with which it may be pushed or pulled to a location, as desired. A further display 52 preferably is carried by the mounting means 14 so as to indicate, to the subject and attendant alike, the level of radioactivity being detected. The three-dimensional adjustability of the mounting means 14 can be effected either manually, pneumatically or electrically by known means, not otherwise disclosed and built into the platform 28. Further, and as illustrated in FIG. 3, the radioactivity detection system 10 also can include two such radioactivity distribution detectors 16 so as to allow analysis of the same event from two detectors 16 viewing the subject with an intersecting angle. Still further, and as illustrated in FIG. 4, a radioactivity detector assembly 54 also can be mounted for rotation about the subject, or in the alternative, a plurality of such detector assemblies 54, shown in dotted lines, can be mounted circumferentially about the subject.

Figure 2:
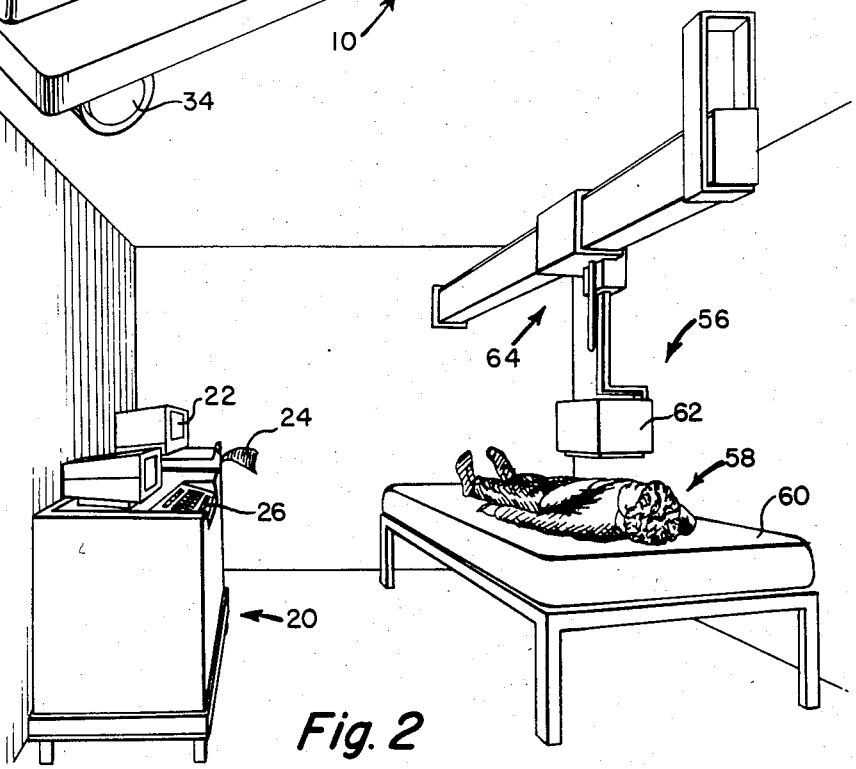
FIG. 2 is a perspective view of another preferred embodiment of a radioactivity detection system constructed in accordance with the present invention.

Another preferred embodiment of a radioactivity detection system 56 is shown in FIG. 2. System 56 is designed for detection of radioactive events in a subject 58 being supine on a table 60, or the like. A radioactivity distribution detector 62 is suspended from a mounting means 64 designed for effecting relative motion between the detector 62 and the subject 58. Such relative motion, both vertical and horizontal, preferably is effected by a suitable electric motor, not shown. Other means, e.g., pneumatic and/or hydraulic, can be employed equally. The radioactivity detection system 56 otherwise is identical with the system 10 shown in and described with reference to FIG. 1 and, as such, fully interfaces with the processing means 20 above described.

Figure 5:
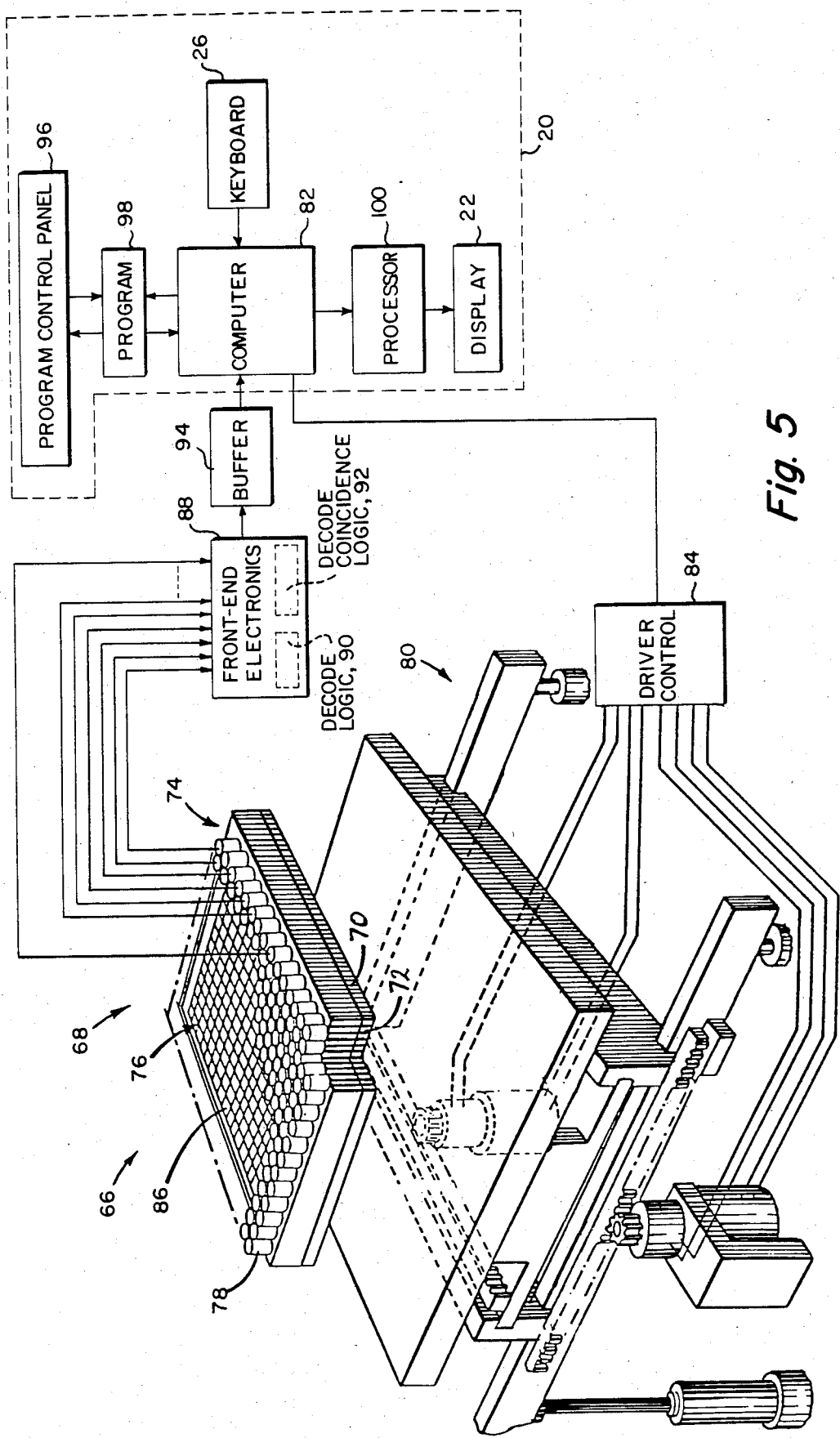
FIG. 5 is a block and schematic diagram of still another preferred embodiment of a radioactivity detection system constructed in accordance with the present invention.

Still another preferred embodiment of a radioactivity detection system 66 is shown in FIG. 5. System 66 comprises a detector assembly 68 which includes a collimator 70 with collimator bores 72, an array 74 of scintillation crystal assemblies 76 and a plurality of superposed light detectors, such as photomultiplier (PM) tubes 78. A subject (not shown) under diagnosis is positioned on a programmable XY platform 80 which is in spaced relation to detector assembly 68, with a portion of the subject being in registration with collimator 70. Responsive to command signals generated by a computer 82 in the processing means 20, scanning signals are generated by a driver control 84 which operates to move the platform 80 in a specified scanning pattern. Conversely, another preferred embodiment would have the detector assembly 68 moving on a programmable XY platform, while the patient remains stationary. A scintillator 86, having a unique address location in the array 74 and being in registration with one collimator bore 72, when activated by securing radioactivity, emits a light signal detected by two adjacent superposed detectors 78. Data signals generated by the detectors 78 first are processed in front-end electronics which includes a decode logic 90 and a decode coincidence logic 92. The decode coincidence logic 92 ensures that data signals have been detected from two, and only two, adjacent detectors 78 which define a unique address for the scintillation event. Events sensed at each unique address are accumulated in a buffer memory 94. Upon completion of each scanning step, the events stored in the buffer memory 94 are fed to the computer 82 in the processing means 20 and the memory 94 cleared for reception of new data. Operation of the radioactivity detection system of whichever above-described embodiment is directed from a control panel 96. Panel 96 preferably is a series of switching devices coupled to the computer 82 via a computer interface 98. Any pertinent data conveniently is logged into the display 22 via the keyboard 26. The data in computer 82 preferably is fed to a microprocessor driven display processor 100 which encodes the scintigraphic data into Gray shade and/or color television signals which drive the visual display 22, which preferably is a raster scan display.

Figure 6:
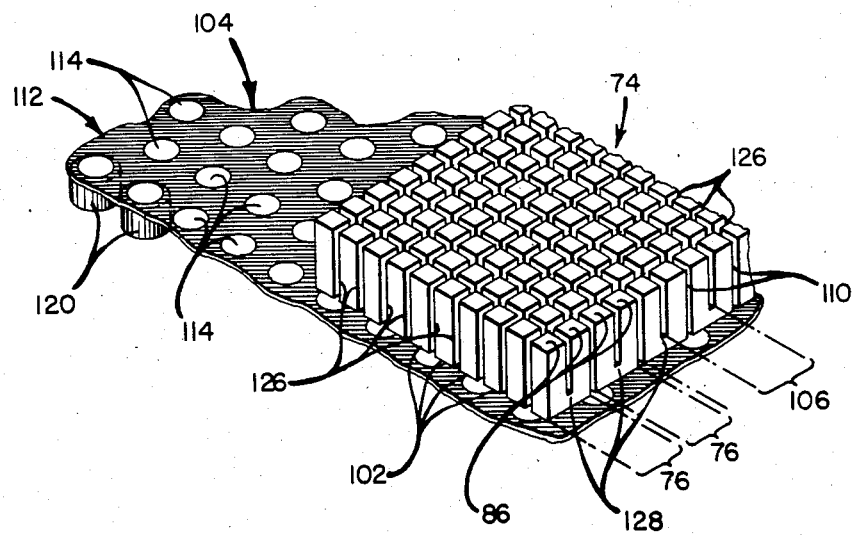
FIG. 6 is a perspective view of a crystal scintillation detector assembly of the radioactivity detection systems illustrated above.
Figure 8:
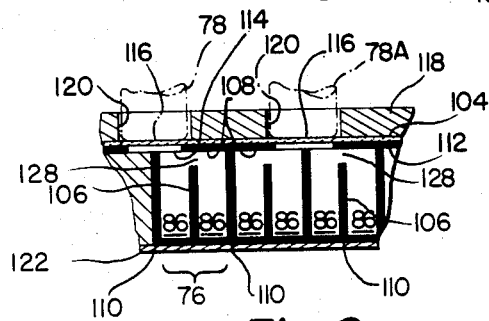
FIG. 8 is a vertical section along the line 8—8 of FIG. 7.

One preferred crystal detector assembly 68 of the radioactivity detection system of whichever above-described embodiment is shown in perspective in FIG. 6. The crystal detector array 74 of assembly 68 comprises a plurality of the scintillation crystal assemblies 76 mounted in parallel rows 102 onto a glass plate 104. Each crystal assembly 76 is formed of a unitary body having a single slot 106 that extends inwardly from one end of the body to define two sensing heads, i.e., scintillators 86, 86. Preferably, each crystal assembly 76 is composed of a scintillation material. Such scintillation material preferably comprises a thallium activiated sodium iodide crystal -NaI(T1), or a cesium iodide crystal -CsI, or a bismuth germanate crystal -$Bi_4 Ge_3 O_{12}$, or the like. The ends of each crystal assembly 76 opposite to the scintillators 86, 86 form two exit windows 108, 108, one each in registration with a corresponding one of the scintillators 86, 86, observe FIG. 8. The slot 106, as well as the openings 110 in between adjacent crystal assemblies 76, are filled with a reflective material, for example magnesium oxide. Further, the glass plate 104 also preferably is selectively coated, as at 112, with a reflective material, except for those areas, as at 114, corresponding to the active internal diameter areas 116 of the PM tubes 78 shown in FIG. 8. Preferably, a plate 118, which may be formed of aluminum or the like, is added to the assembly 68 and glued to the glass plate 104 on the side facing the PM tubes 78. The primary function of this plate 118 is to add structural strength and rigidity to the assembly 68 and to provide proper and accurate positioning of the PM tubes 78 within appropriate locating holes 120. It will be observed in FIG. 8 that these locating holes 120 are formed with diameters slightly larger than the outside diameters of the PM tubes 78 so that the tubes 78 may fit snugly therein. A cover plate 122, added on the radiation entrance side, completes the crystal detector assembly 68 and serves as the radiation entrance window thereof. Preferably, the cover plate 122 also is formed of a material with a minimal radiation attenuation coefficient for gamma rays of 50 KeV and greater, e.g., aluminum.

The array 74 of crystal assemblies 76 may be made in any convenient manner. For example, a slab of scintillator material first is prepared to the required dimensions. Next, a series of equidistantly placed parallel channels 126 are cut in the slab, preferably all the way through so as to form the parallel rows 102. Then, in a direction normal to the direction of the channels 126, the slots 106 and the openings 110 are alternately cut in the slab so as to form the plurality of crystal assemblies 76. It will be noted that the openings 110 preferably are cut all the way through, but not the alternate slots 106, so as to leave a bridge 128 of scintillator material preferably adjacent the exit windows 108, 108 in each crystal assembly 76. The significance of this bridge 128 and its thickness will be more fully described below. Thereafter, the slots 106, the openings 110 and the channels 126 preferably are filled with the reflective material, and the cover plate 122 secured in place.

Figure 7:
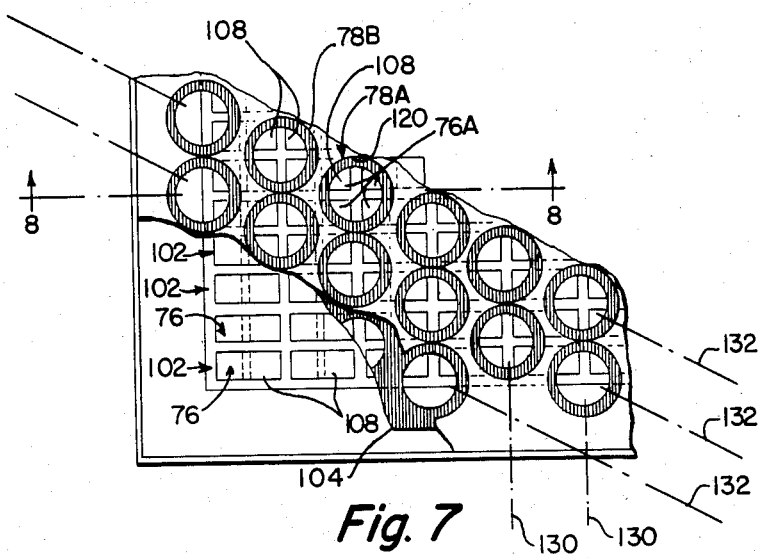
FIG. 7 is a schematic diagram showing one preferred positional relationship between a plurality of crystal scintillator assemblies and a plurality of light detectors.

One preferred positional relationship between a plurality of crystal assemblies 76 and a plurality of light detectors 78 of the crystal detector assembly 68 is shown schematically in FIG. 7. Other preferred positional relationships between the crystal assemblies and the light detectors are shown, respectively, in FIGS. 9 and 11. The underlying principle, which we call the doublet principle, however is the same for each of these illustrated preferred positional relationships. This doublet principle provides the radioactivity detection system of the invention in each of the above-described embodiments with a simple coding scheme. According to this coding scheme, light generated by a scintillation in one scintillator 86 of one crystal assembly 76 is designed to fall on, and thus activate, two adjacent light detectors, e.g., PM tubes 78, but with one PM tube 78 receiving more light than the other.

Figure 13:
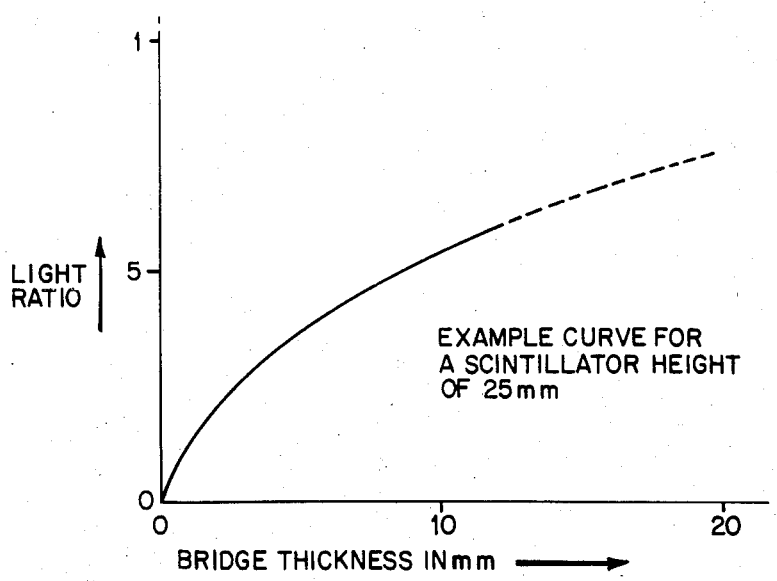
FIG. 13 is a graph illustrating certain principles of the present invention.

As will be evident from viewing the respective drawings, one PM tube 78A is associated with four crystal assemblies 76A, with each assembly 76 comprised of two scintillators 86, 86, that is eight scintillator crystals altogether. Of these eight scintillators 86, four scintillators 86 are directly underneath the PM tube 78A and four scintillators 86 are moved over one position. These four, one position removed scintillators 86, are respectively associated with four adjacent PM tubes 78. A scintillation occurring in one of the four scintillators 86 directly underneath the PM tube 78A casts more light on that PM tube 78A than on the adjacent PM tube 78B, and it causes no light to be cast on any other PM tube 78. The emission of a lesser amount of light from the scintillator 86 found directly underneath the PM tube 78A on the adjacent PM tube 78B is effected by the bridge 128 of scintillation material, which in fact physically connects and optically couples the two adjacent scintillators 86, 86 into the one crystal assembly 76, observe FIG. 8. The thickness of this bridge 128 above the slot 106 relative to the height of the crystal scintillators 86, 86 governs the light distribution between the two adjacent PM tubes 78A and 78B. The ratio of bridge 128 thickness to scintillator 86 height must always be greater than zero. In FIG. 13, there is illustrated the variation of the light distribution with the thickness of the bridge 128, with the bridge 128 funcioning as a light mixer. FIG. 13 plots the light ratio versus the thickness of the bridge 128. The light ratio is defined for the example PM tubes 78A and 78B as the amount of light received by 78B divided by the amount of light received by tube 78A. As may be observed therein, the light ratio always should be less than one under all conditions, keeping in mind statistical fluctuations. The light ratio must be large enough, however, to assure that the electrical signals from both PM tubes 78A and 78B are sufficiently high so as to exceed anticipated noise levels in background or in the processing circuitry.

The preferred positional relationship as depicted in FIG. 7 is achieved by arranging the PM tubes 78 in parallel rows 130 running in a direction normal to the parallel rows 102 of the crystal assemblies 76, and in further parallel rows 132 running at an angle to both the row 130 and the rows 102.

Figure 9:
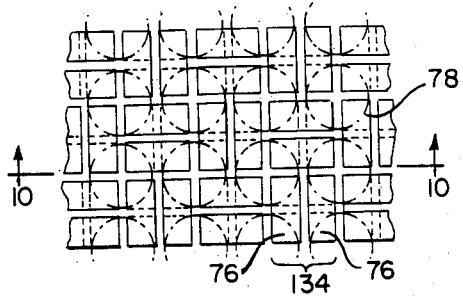
FIG. 9 is a schematic diagram showing another preferred positional relationship between a plurality of crystal scintillator assemblies and a plurality of light detectors.
Figure 10:
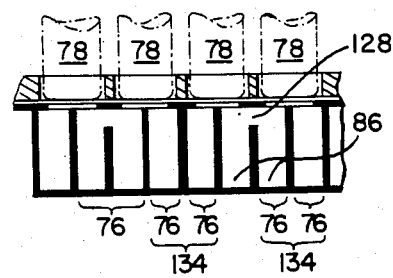
FIG. 10 is a vertical section along the line 10—10 of FIG. 9.

The second preferred positional relationship between a plurality of crystal assemblies 76 and a plurality of light detectors 78 is depicted in FIGS. 9 and 10. In this arrangement, preferably a pair of crystal assemblies 76 are mounted in one can 134, with adjacent cans 134 disposed normal to one another. The PM tubes 78, oh the other hand, are disposed in parallel rows in two directions normal to one another.

Figure 11:
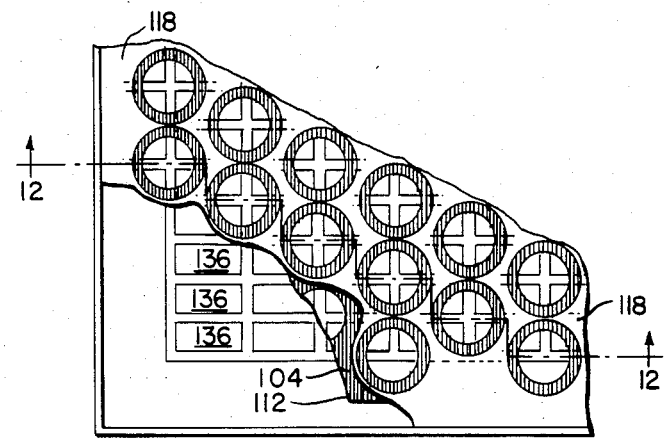
FIG. 11 is a schematic diagram similar to the one shown in FIG. 7 but illustrating a different embodiment of the present invention.
Figure 12:
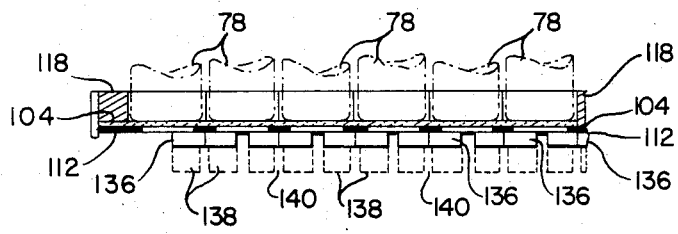
FIG. 12 is a vertical section along the line 12—12 of FIG. 11.

In FIGS. 11 and 12, there is illustrated a still further embodiment of the present invention. The positional arrangement is similar to that shown in FIG. 7, but in lieu of the crystal assemblies 76, a plurality of wafers 136 are used. The wafers 136 also are formed of a scintillation material, and they may optionally also include a pair of scintillators 138, 138. If so, the slot 140 between the scintillators 138, 138 preferably also is filled with a reflective material, not shown. The height of the scintillators 138 can vary from a theoretical zero to some positive value, although it would always be somewhat less than the maximum height of the scintillators 86. The embodiment shown in FIGS. 11 and 12 particularly is useful for low energy isotopes which characteristically require less scintillation material so as to generate a photon therein. This embodiment also incorporates the doublet principle above mentioned in that the light of a scintillation in half of one wafer 136 is detected by two adjacent PM tubes 78, with one detector receiving more light than the other. The front-end electronics 88 will register the corresponding electrical signals generated by the two adjacent PM tubes 78 only if one signal is greater than the other and will reject all other signals as invalid.

Thus it has been shown and described an improved high resolution radioactivity detection system 10 designed for presentation of radioactive event distributions, which system 10 satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A radioactivity distribution system for stress analysis of a subject comprising:
   (a) an exercising means;
   (b) said exercising means being an exercise bike worked about a vertical axis passing through the heart of said subject;
   (c) mounting means secured on a platform and releasably connected to said exercising means;
   (d) said mounting means being separately three-dimensionally adjustable;
   (e) a radioactivity distribution detector secured on said mounting means for three dimensional adjustability thereof;
   (f) processing means separately mounted from said mounting means but being operatively coupled to said radioactivity distribution detector and including a display means for processing and presenting a representation of radioactivity distribution within said subject; and
   (g) a recording means for recording said representation of radioactivity distribution within said subject.

2. The radioactivity distribution system of claim 1 wherein said detector includes a plurality of scintillators and superposed detectors, said system further comprises a yoke rotatably journalled to said mounting means and a second radioactivity distribution detector also secured on said mounting means.

3. A radioactivity distribution system for stress analysis of a subject comprising:
   (a) an exercising means;
   (b) mounting means secured on a platform and releasably connected to said exercising means;
   (c) a radioactivity distribution detector secured on said mounting means;
   (d) said exercising means being an exercise bike worked about a vertical axis passing through the heart of said subject;
   (e) a yoke rotatably journalled to said mounting means;
   (f) said mounting means being separately three-dimensionally adjustable, with said adjustability being effected manually; and
   (g) a second radioactivity distribution detector also secured on said mounting means.

* * * * *